(12) United States Patent
Elston et al.

(10) Patent No.: US 7,407,652 B2
(45) Date of Patent: Aug. 5, 2008

(54) PROBIOTIC SYSTEM FOR AQUACULTURE

(75) Inventors: Ralph A. Elston, Carlsborg, WA (US); Arthur Gee, Tacoma, WA (US); Karen L. Humphrey, Sequim, WA (US)

(73) Assignee: AquaTechnics Inc., Seguim, WA (US)

( * ) Notice: Subject to any disclaimer, the term of this patent is extended or adjusted under 35 U.S.C. 154(b) by 71 days.

(21) Appl. No.: 11/144,929

(22) Filed: Jun. 3, 2005

(65) Prior Publication Data

US 2006/0275324 A1  Dec. 7, 2006

(51) Int. Cl.
  *A01N 63/00* (2006.01)
  *C12N 1/00* (2006.01)
  *C12N 1/12* (2006.01)
  *C12N 1/20* (2006.01)

(52) U.S. Cl. .................. 424/93.4; 435/252.1; 435/243; 435/822

(58) Field of Classification Search ........................ None
  See application file for complete search history.

(56) References Cited

FOREIGN PATENT DOCUMENTS

| JP | 2001-293444 | * | 3/2001 |
|---|---|---|---|
| JP | 2001224363 | * | 8/2001 |

OTHER PUBLICATIONS

Holstrom et al "Marine Pseudoalteomonas sp. are associated with higher organisms and product bio. active extracel. agents", Fems Microb. Eco., vol. 30, No. 4, Dec. 1999, pp. 285-293.*

Kon-Ya K et al, "Inhib. effect of bac. ubiquinones on settling of barnacle, . . . " Experientia (Basel), vol. 51, No. 2, 1995, pp. 153-155.*

Estes, Robyn, M., et al., "Pathogenicity testing of shellfish hatchery bacterial isolates on Pacific oyster *Crassostrea gigas* larvae," Diseases of Aquatic Organisms, 58:223-230, 2004.

Elston, Ralph, et al., "Progress in the development of effective probiotic bacteria for bivalve shellfish hatcheries and nurseries," Abstract from Pacific Coast Shellfish Growers Association annual meeting, Portland, Oregon, Oct. 8-11, 2003.

Elston, Ralph A., et al., "Extrapallial abscesses associated with chronic bacterial infections in the intensively cultured juvenile Pacific oyster *Crassostrea gigas*," Diseases of Aquatic Organisms, 37:115-120, 1999.

Elston, R, et al., "Conchiolin infection and surface coating *Vibrio*: shell fragility, growth depression and mortalities in cultured oysters and clams, *Crassostrea virginica*, *Ostrea edulis* and *Mercenaria mercenaria*," Journal of Fish Diseases, 5:265-284, 1982.

Elston, R., et al. "Pathogenesis of Experimental Vibrosis in Larval American Oysters, *Crassostrea virginica*," Can. J. Fish. Aquat. Sci., 37:964-978, 1980.

Elston, Ralph, et al., "Progress in the Development of Effective Probiotic Bacteria for Bivalve Shellfish Hatcheries and Nurseries," WAS Honolulu, 2004.

Elston, Ralph, et al., "Recent Advantages in Disease Management for Intensive marine Mollusc Culture," 1980.

Elston, Ralph, et al., "Bacterial Management in Shellfish Hatcheries," AES Presentation Abstract, AES Issues Forum, Nov. 2003.

* cited by examiner

*Primary Examiner*—David M. Naff
*Assistant Examiner*—Deborah K. Ware
(74) *Attorney, Agent, or Firm*—Jane E. R. Potter; Davis Wright Tremaine LLP

(57) ABSTRACT

Probiotic bacterial strains are provided which inhibit or prevent growth or pathogenic bacteria in marine organisms. Also provided are methods of culturing marine organisms using the probiotic bacteria.

18 Claims, 11 Drawing Sheets

PROBIOTIC SYSTEM FOR AQUACULTURE

FIELD OF THE INVENTION

The invention relates to novel bacterial strains useful for the inhibition of growth of pathogenic bacteria in marine organisms.

BACKGROUND OF THE INVENTION

Since the mid-1970's, the bivalve mollusk (oysters, clams, scallops and related species) aquaculture industry has become increasingly intensified, particularly on the west and east coasts of the United States, and more recently, efforts toward hatchery development are also taking place on the Gulf coast. Previously (and still, in some areas), the edible market industry for these products depended on wild reproduction and natural recruitment into extensively harvested populations. High variability in the supply and quality of natural bivalve seed motivated research and development to establish technology for the intensive management of brood stock, reproduction and rearing of bivalves, at least through early seed stages. Thus today, the industry in many locations on both the west and east coasts is based largely on an intensive agricultural production model, although there are many modes and methods for the grow out of marketable product. However, there remains a very significant need and opportunity to markedly improve the efficiency of various components in the production cycle, as well as address the unique problems inherent for each new species brought into aquaculture.

Although the bivalve shellfish seed production industry, even for the longest cultured species such as oysters, operates on a commercial scale, the consistency of production is still highly variable and a great scope for improvement of efficiency exists. One of the most serious challenges has always been the management of aggressive opportunistic bacterial infections in larval and juvenile cultures. One reason that these diseases have not been uniformly and effectively managed by sanitation and health management procedures is because the bacterial colonization of culture systems remains an uncontrolled variable. Sometimes the benign bacteria colonize the system but often pathogens or a population of bacteria that are antagonistic in some way to the cultured animals establish dominance and result in low productivity and high variability in the success of culture batches.

Opportunistic infections are even more significant in the culture of seed or juvenile bivalves than in larvae. Different shellfish species have variable susceptibility to these bacterial infections. Many, but not all of these infections, are caused by Vibrio spp. (Elston et al. 1999). Elston (1999) identified a variety of instances in which bacterial diseases were causal in larval and seed oyster mortalities. Chronic bacterial diseases of bivalve seed are especially insidious and often go unrecognized as a bacterial disease, even though the cumulative mortality may, in some cases, approach 100% (Elston et al. 1999) and poor growth and discarded substandard seed dramatically compound the losses. In addition, a syndrome of seed oyster losses along the northeast coast of the United States referred to as juvenile oyster disease (JOD), that affects seed of the Eastern oyster, *Crassostrea virginica*, appears to have a bacterial etiology (Boettcher et al., 2000). Current experience with commercial nursery losses shows that bacterial diseases of the Pacific oyster (*Crassostrea gigas*), Kumomoto oyster (*Crassostrea sikamea*), and geoduck clam (*Panope abrupta*) seed can be highly destructive. The primary mode of pathogen invasiveness, especially for larval and seed oysters, is the progressive growth of bacteria from the oyster shell surface into the soft tissues (Elston et al. 1982, Elston et al. 1999) although there is limited documentation of gastrointestinal bacterial abscesses (Elston and Leibovitz 1980) and the role of bacteria in the water column and associated with algal cultures is not well understood.

Based on the findings described above, there is a significant need in the art for compositions and methods to treat and or prevent pathogenic bacterial infections in marine orgamsms.

SUMMARY OF THE INVENTION

One embodiment provides a biologically pure bacterial strain of bacteria *Pseudoalteromonas* P02-1 deposited as ATCC PTA-6677, *Pseudoalteromonas* P02-45 deposited as ATCC PTA-6678, or a mixture thereof.

Further embodiments provide variants of the bacterial strains bacterial strains P02-1 and P02-45, alone or in combination, that inhibit colonization by pathogenic or antagonistic bacteria in marine organisms.

Still further embodiments include methods of inhibiting a pathogenic bacterial infection in marine organisms, comprising bathing a stock of marine organisms in a culture containing probiotic bacterial strains P02-1 and P02-45, alone or in combination.

Other embodiments include methods to treat cultured marine organisms, including but not limited to mollusks, shrimp, cultured food fish, and marine aquarium fish at all growth stages.

Another embodiment provided herein is a method of preventing growth of pathogenic bacteria by treatment of marine organism rearing tanks with probiotic bacterial strains prior to the introduction of marine organisms to the tank.

The invention also provides compositions comprising probiotic bacterial strains and cultures of unicellular algae or multicellular algae, where the combination of bacterial strain and algae are used to feed marine organisms.

In another embodiment, the invention provides a method of preventing growth of pathogenic bacteria in commercial and residential salt water aquariums wherein the aquarium is treated with bacterial strain P02-1, P02-45, or a mixture thereof.

Provided is a biologically pure bacterial strain of bacteria *Pseudoalteromonas* P02-1 deposited as ATCC PTA-6677. Also provided is a biologically pure bacterial strain of bacteria *Pseudoalteromonas* P02-45 deposited as ATCC PTA-6678.

Further provided are a variant of the bacterial strain of bacteria *Pseudoalteromonas* P02-1 deposited as ATCC PTA-6677 wherein the variant strain has a protective property against colonization of marine organisms by pathogenic bacteria, and a variant of the bacterial strain bacteria *Pseudoalteromonas* P02-45 deposited as ATCC PTA-6678 wherein the variant strain has a protective property against colonization of marine organisms by pathogenic bacteria.

Still further provided is a composition comprising a mixture of bacterial strains *Pseudoalteromonas* P02-1 and *Pseudoalteromonas* P02-45 wherein the mixture contains between 1% and 99% colony forming units of strain *Pseudoalteromonas* P02-1 and between 1% and 99% colony forming units of strain P02-45.

Also provided is a method of inhibiting a pathogenic bacterial infection in marine organisms, comprising bathing a stock of marine organisms in a culture containing a bacterial strain of the invention; the marine organisms may be mollusks, and may be *Artemia* spp., including *Artemia franciscana* and *Artemia salina*, *Brachionus* spp., including *Bra-*

*chionus plicatilis*, or may be marine shrimp including but not limited to the genera *Litopenaeus, Farfantepenaeus* and *Penaeus*; the marine organisms may be cultured food fish, including but not limited to salmon, trout, grouper, tuna fishes and all marine species whose early life stages may be reared under controlled conditions in seawater hatcheries and nurseries; the marine organisms may be in the nauplii, larval, post-larval, or juvenile stage, or may be adults or brood stock, and the concentration of the bacterial strain may be between $10^3$ to $10^7$ colony forming units per mL of culture.

Also provided is a method of inhibiting a pathogenic bacterial infection in marine organisms, comprising bathing a stock of the marine organisms in a culture containing a composition; the marine organisms may be mollusks, and the marine organisms may be *Artemia* spp., including *Artemia franciscana* and *Artemia salina*, *Brachionus* spp., including *Brachionus plicatilis*, or may be marine shrimp including but not limited to the genera *Litopenaeus, Farfantepenaeus* and *Penaeus*; the marine organisms may be cultured food fish, including but not limited to salmon, trout, grouper, tuna fishes and all species whose early life stages may be reared under controlled conditions in seawater hatcheries and nurseries; the marine organisms may be in the nauplii, larval, postlarval, juvenile stage or adult stage, or may be a brood stock; the total concentration of the mixture of bacteria may be between $10^3$ to $10^7$ colony forming units per mL of culture.

Still further provided is a method of preventing growth of pathogenic bacteria by treatment of marine organism rearing tanks with bacterial strain of the invention, or a composition comprising a mixture of bacterial strains *Pseudoalteromonas* P02-1 and *Pseudoalteromonas* P02-45 wherein the mixture contains between 1% and 99% colony forming units of strain *Pseudoalteromonas* P02-1 and between 1% and 99% colony forming units of strain P02-45, prior to the introduction of marine organisms to the tank.

Further provided is a composition comprising at least one bacterial strain of the invention and a culture of unicellular algae; the unicellular algae may be selected from the group consisting of *Tahitian Isochrysis galbana, Chaetoceras calcitrans, Tetraselmis* sp., strain 429, and *Thallasiosira pseudonana*; the unicellular algae may also be selected from the group consisting of *Rhodomonas* sp., *Tetraselmis* sp., strain Plat P, *Skeletonema costatum, Skeletonema* spp., *Pavlova lutheri, Isochrysis* spp., including Caribbean *Isochrysis* sp., *Chaetoceras* spp, *Navicula inerta* and other *Navicula* spp., *Nitzschia ovalis, Nitzschia closterium, Nitzshia laevis* and other *Nitzschia* spp., *Amphora coffeaeformis* and other unicellular algae useful for feeding cultured mollusks; the bacterial strain and unicellular algae may be co-cultured; in some embodiments the at least one bacterial strain is a composition comprising a mixture of bacterial strains *Pseudoalteromonas* P02-1 and *Pseudoalteromonas* P02-45 wherein the mixture contains between 1% and 99% colony forming units of strain *Pseudoalteromonas* P02-1 and between 1% and 99% colony forming units of strain P02-45.

Further provided is a composition comprising at least one bacterial strain of the invention and a culture of multicellular algae; the at least one bacterial strain may be a composition comprising a mixture of bacterial strains *Pseudoalteromonas* P02-1 and *Pseudoalteromonas* P02-45 wherein the mixture contains between 1% and 99% colony forming units of strain *Pseudoalteromonas* P02-1 and between 1% and 99% colony forming units of strain P02-45; the multicellular algae may be selected from the group consisting of *Palmaria mollis, Laminaria* spp., *Macrocystis pyrifera* and other *Macrocystis* spp., *Gracilaria* spp., *Ulva* spp., *Nereocystis* spp, *Lithothanmnium californicum* and other *Lithothamnium* spp., and other multicellular or macro-algae useful for feeding cultured mollusks; the bacterial strains and the unicellular algae may be co-cultured.

Still further provided is a method of preventing growth of pathogenic bacteria in commercial and residential salt water aquariums wherein the aquarium is treated with bacterial strain P02-1, P02-45, a variant thereof, a mixture thereof, or a composition comprising a mixture of bacterial strains *Pseudoalteromonas* P02-1 and *Pseudoalteromonas* P02-45 wherein the mixture contains between 1% and 99% colony forming units of strain *Pseudoalteromonas* P02-1 and between 1% and 99% colony forming units of strain P02-45; the marine organisms in the aquarium may be in the nauplii, larvae, post-larvae or juvenile stage or may be adults or brood stock.

DETAILED DESCRIPTION OF THE INVENTION

Introduction

Figure 1:
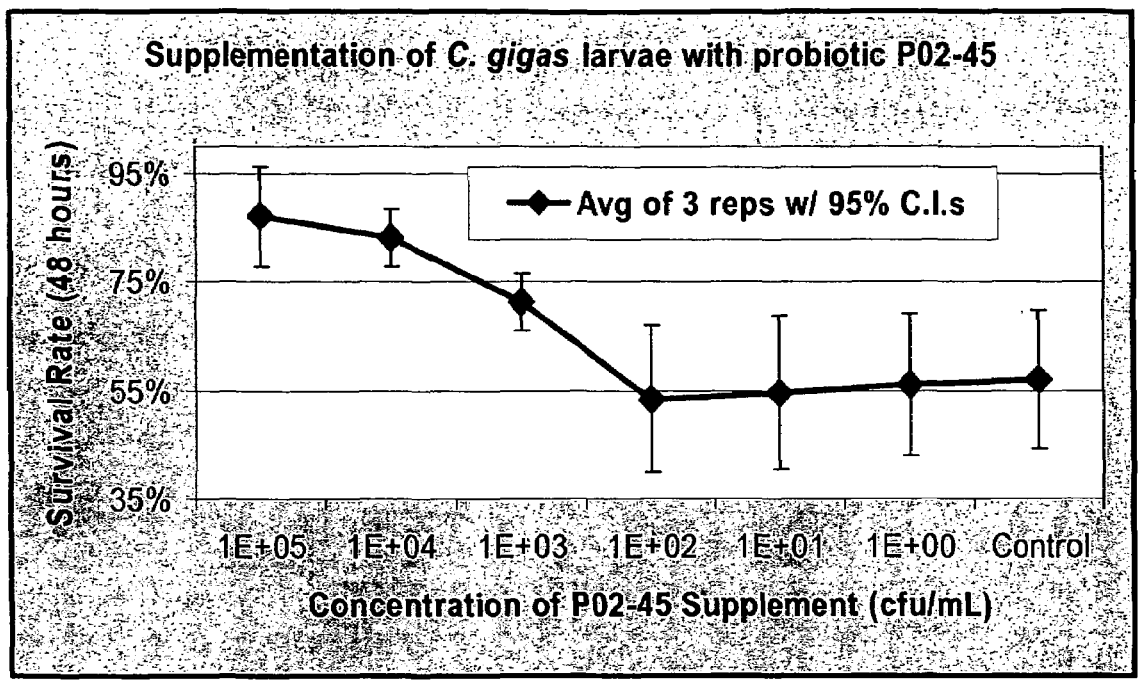
FIG. 1 shows that supplementation of Pacific oyster larval cultures (12 day old) with probiotic P02-45 increases survival. The figure is representative of multiple experiments. Improved survival was demonstrated at concentrations of between $10^3$ and $10^5$ cfu/mL.

The invention relates to the use of probiotic bacteria to inhibit or prevent growth of pathogenic bacteria in marine organisms and cultures thereof. Two bacterial strains, P02-1 and P02-45, have been isolated and evaluated for their effectiveness in inhibiting pathogenic bacterial growth and in promoting the survival of marine organisms. The primary objective of introducing beneficial or benign bacteria to occupy the culture system surfaces and bivalve shell surfaces is a rational approach. Ingestion of such benign or beneficial bacteria may have additional benefits by controlling colonization of the gastro-intestinal tract and contributing to nutrition. Although the data disclosed herein pertain to bivalve mollusks, this approach may be useful for any marine aquaculture system.

The term "probiotic bacteria" refers to bacterial strains that when fed to or used to inoculate or treat animals or marine organisms or their holding tanks when they are cultivated, and to inhibit, reduce, and/or prevent colonization by pathogenic bacteria. The term "pathogenic bacteria" refers to bacterial strains that cause disease, reduce growth, condition or health or are antagonistic to optimizing growth health or condition when marine animals are cultivated. Probiotic bacteria include strains P02-1, P02-45 and variants thereof, either individually or in combination. Variants may be identified in a non-limiting manner by, for example, belonging to the same genus and exhibiting a fatty acid profile characterization profile similar to that of P02-1 or P02-45.

The term "marine organisms" refers to organisms that can survive, breed, and/or live in salt water, and/or are native to an ocean. Marine organisms include but are not limited to mollusks, edible marine shrimp (*Litopenaeus, Farfantepenaeus*, and *Penaeus*), cultured food fish (such as salmon, trout, grouper, tuna fishes and all marine species whose early life stages may be reared under controlled conditions in seawater hatcheries and nurseries), saltwater aquarium fish, species that are used to feed marine shrimp (*Artemia* spp., including *Artemia franciscana* and *Artemia salina*) and species that are used to feed edible marine fish species (*Brachionus* spp., including *Brachionus plicatilis*, commonly known as rotifers).

The term "mollusk" includes but is not limited to organisms in the classes bivalvia (clams, oysters, scallops, mussels), gastropoda (abalone, snails, slugs, limpets), and cephalopoda (squids, octopuses, nautilus, cuttlefish). Of the bivalves, species that have been the subject of studies involving pathogenic bacterial infection include the Eastern oyster (*Crassostrea virginica*), the Pacific oyster (*Crassotrea gigas*), Kumomoto oyster (*Crassotreasikamea*), geoduck clam (*Panope abrupta*), and Manila clam (*Venerupis philippinarium*).

Marine organisms may be treated with probiotic bacteria at a variety of life stages, including fertilized eggs, the larval stage (in salmon and trout, these may be called sac-fry or fry), metamorphic stage, adult stage, as well as organisms that are brood stock (adult stage, reproductive organisms that have been conditioned to spawn). One optional mode of treatment, which applies to marine organisms, including mollusks, shrimp, and fish, is to treat most or all stages of growth, from the brood stock, through egg spawning and fertilization, and then through juvenile stages.

For marine shrimp species, the life stages comprise fertilized eggs, larvae (developmental stages include nauplier, protozoel, and mysis), postlarval, juveniles, sub-adults, spawning adults, and non-spawning adults.

Brood stocks of marine organisms may be treated with probiotic bacteria prior to spawning. Conditioned brood stock are washed and prepared for spawning according to normal hatchery operations procedures. The brood stock can be bathed in a suspension of single or multiple probiotic bacteria adjusted to a bacterial concentration of between $1\times10^3$ and $1\times10^7$ cfu/mL. This bath treatment is initiated when the marine organisms are placed in spawning trays with the intent that the brood stock will pump the probiotic-containing water through their water tubular system and provide a treatment of the ova and sperm with the probiotic bacteria. This treatment may be combined with other treatments.

In order to coat their shells with probiotic bacteria, marine organisms in various growth stages may be treated with probiotic bacteria during the processes of screening and grading. Screening is defined as a process in which early life stage marine organisms in a tank are split into several tanks to prevent crowding, or alternatively, when the tanks are cleaned. Grading is defined as a part of the screening process in which the marine organisms are screened through progressive mesh sizes of screens to separate them by size. Larvae from static or continuous culture tanks can be treated when concentrated by screening for tank cleaning or grading. In static culture tanks, this typically occurs every two to three days but in continuous culture tanks, draining and grading occurs less frequently (3 to 6 day intervals). The concentrated larvae are resuspended in a minimal volume of sterile seawater (SSW) containing probiotic bacteria at a concentration of from $1\times10^3$ to $1\times10^7$ cfu/mL for 10 minutes to 1 hour. Untreated control larvae from separate tanks can be used and quantitatively characterized (survival, growth, time to metamorphosis) in parallel with the treatment group. Alternatively, or in addition, tanks used in these processes can be treated prior to the addition or transfer of marine organisms.

Addition of probiotic strains to concentrated cultures of oyster seed reared in upwellers can be carried out as follows. Upwellers are devices (cylindrical tubes with a screen, inside a flowing water box) that are used in mollusk culture. The devices can be used either as upwellers or downwellers depending on the direction of the plumbing. When the larvae stage is nearly completed, the larvae tend to stop swimming and sink to the bottom. However, this is not perfectly synchronized in a population. When larvae are transferred out of a larval growth tank, they are transferred to the device set up as a "downweller" which means the water flow is downward, tending to push the larvae down onto the retaining screen in the bottom of the cylinder, thus preventing those with a tendency to still swim from going up too far in the cylinder and out the overflow pipe. Once the population has settled, has completed metamorphosis, and is predominantly or entirely non-swimming, the device is converted to an upweller by switching the plumbing. This allows an increasing capacity of biomass to be maintained in the cylinder, with the screen in the cylinder as a base. The upwelling current, containing food particles, is adjusted to "fluidize" the mass of small shellfish so that they tend to tumble in the upweller, providing for good distribution of food. There are other devices that are used for these life stages but all generally work on a similar principle.

Metamorphic and juvenile oysters up to about 3 mm shell length may be treated with probiotic bacteria in concentrated probiotic suspensions similar to that described for treatment of larval oyster suspensions. These oysters will be metamorphic animals or juveniles that are reared as "singles" in a convertible downweller/upweller system. Specifically, the concentrated juveniles can be resuspended in a minimal volume of SSW containing probiotic bacteria at a concentration of from $1\times10^4$ to $1\times10^5$ cfu/mL for 10 minutes to 1 hour. Untreated control larvae from separate tanks are used and quantitatively characterized (survival and growth) in parallel with the treatment group. Adult organisms may also be similarly treated with probiotic bacteria at concentrations of $1\times10^3$ to $1\times10^7$ cfus per mL of culture solution.

Tanks and upwellers may be re-treated to maintain a stable culture of the probiotic bacteria. One method for treating static culture tanks is to treat the tanks after each round of draining and cleaning, while the marine organisms are concentrated. For continuous culture tanks, probiotic may be added to the culture tank water at intervals from one to three days. This may be accomplished by turning off the water flow for up to one hour after the addition of probiotic bacteria at the concentration indicated previously. During this time, the probiotic bacteria may attach to larval shells and tank surfaces or possibly be ingested by larvae.

Pretreatment of vessels used for growth of marine organisms can be accomplished as follows. In addition to establishing a stable population of probiotic bacteria on the external shell surface of larvae and juveniles, it may be beneficial to establish a population of probiotic bacteria on the surfaces of the culture system. A method to promote colonization of marine organisms with probiotic bacteria is to pre-treat vessels that the organisms will be grown in, with the objective of coating the walls and floor of the tanks with the probiotic bacteria to reduce or preempt colonization by antagonistic or pathogenic bacteria. Residual bacteria in the water column may be beneficially taken up by larvae or attach to larval shells. To this end, larval rearing tanks may be pretreated with probiotic bacteria. The tanks used to rear Pacific oyster larvae are generally in the range of 32,000 L to 40,000 L, but larger or smaller tanks may also be suitable and smaller tanks are now being introduced into commercial culture of this species. In order to treat a 40,000 L tank with an initial suspension of $1\times10^5$ cell cfu/mL, a suspension of 40 mL of bacteria containing about $1\times10^{11}$ cells would be suitable.

Alternatively, upwellers and downwellers may be pretreated with probiotic bacteria. Downweller/upweller tubes and the box systems that hold them in the nurseries may be treated for one hour in a static condition with probiotic suspensions at comparable concentrations used to treat larval tanks. This treatment may be repeated, as well as combined with other treatments.

Addition of probiotic bacteria to selected algal feeds in batch and continuous (bag) cultures used for feeding both larvae and juvenile oysters can be accomplished as follows. Because probiotic bacteria have been shown to be compatible with and may enhance the growth rate of unicellular algal feeds, bacteria may be added to algal cultures in the hatchery and then used to feed larvae and juveniles. A number of species of unicellular algae have been shown to be useful for feeding marine organisms. They include but are not limited to Tahitian *Isochrysis galbana*, *Chaetoceras calcitrans*, *Tetraselmis* sp., strain 429, and *Thallasiosira pseudonana* (commonly known as "3H"), *Rhodomonas* sp. (known commonly as "3C"), *Tetraselmis* sp., strain Plat P, *Skeletonema costatum*, *Skeletonema* spp., *Pavlova lutheri*, *Isochrysis* spp., including Caribbean *Isochrysis* sp., *Chaetoceras* spp, *Navicula inerta* and other *Navicula* spp., *Nitzschia ovalis*, *Nitzschia closterium*, *Nitzshia laevis* and other Nitzschia spp., *Amphora coffeaeformis* and other unicellular algae useful for feeding cultured marine organisms.

The probiotic strains can be added to static or continuous (bag) cultures of unicellular algae. In continuous, or bag cultures, nutrients and water are added continuously to the growth vessel to maintain stable conditions in the vessel while algae growth is occurring, providing a continuous harvest of algae rather than individual batches as in static cultures. These type of cultures allow algae to grow at a relatively continuous growth rate. Probiotic species can be added to continuous (bag) cultures and static cultures of algae used for both early larval rearing and species used for older larval rearing and for juvenile rearing.

Algal concentrations are monitored using a Coulter Counter and bacterial concentration by plate dilution through the culture cycle to measure the effect of the addition of probiotic bacteria on the viability of long term (bag or continuous) cultures or the optimal harvest time of static cultures. Bag cultures are inoculated both at startup and later in the algal growth cycle, and static cultures at the flask or carboy stage, early in the scale up cycle. Additionally, $CO_2$ may be used to enhance the growth of the algal and bacterial cultures. These feeds may be administered to larval marine organisms in tanks and juvenile oysters in upwellers.

Addition of probiotic strains to multicellular algae feed strains is carried out as follows. Multicellular algae (otherwise known as macroalgae) may also be used to feed marine organisms including gastropods (such as abalone, *Aplysia californica*), and cephalopods. The multicellular algae include but are not limited to the following species: *Palmaria mollis* (otherwise known as dulse), *Laminaria* spp., *Macrocystis pyrifera* and *Macrocystis* spp., *Gracilaria* spp., *Ulva* spp., *Nereocystis* spp, *Lithothanmnium californicum* and *Lithothamnium* spp.

Marine fish in both commercial and home aquariums may be treated with probiotic bacterial strains. Due to their confinement in a controlled environment, it is possible to treat such organisms at all life stages. The tanks may be treated with $10^3$ to $10^7$ cfus of probiotic bacteria per mL of water.

The following examples are offered by way of illustration, and not by way of limitation.

EXAMPLES

Example 1

Addition and Recovery of Probiotic Bacteria in Larval and Juvenile Cultures

Larval and juvenile Pacific oysters (*Crassostrea gigas*) were used in most experiments as indicated while other larval bivalves were used in some experiments to evaluate any unintended pathogenicity of the probiotic isolates. We exposed larval and juvenile oysters to test for tolerance to the probiotic and recovery from the cultures. We found that at doses from $10^3$ to $10^6$ probiotic (P02-45 and P02-1) colony forming units (cfu) per mL, larval survival in unchallenged treatments was statistically improved over controls (FIG. 1). In addition, to bracket the upper limit of tolerance of larvae or detect possible pathogenicity, we also tested Manila clam (*Venerupis*

Figure 2:
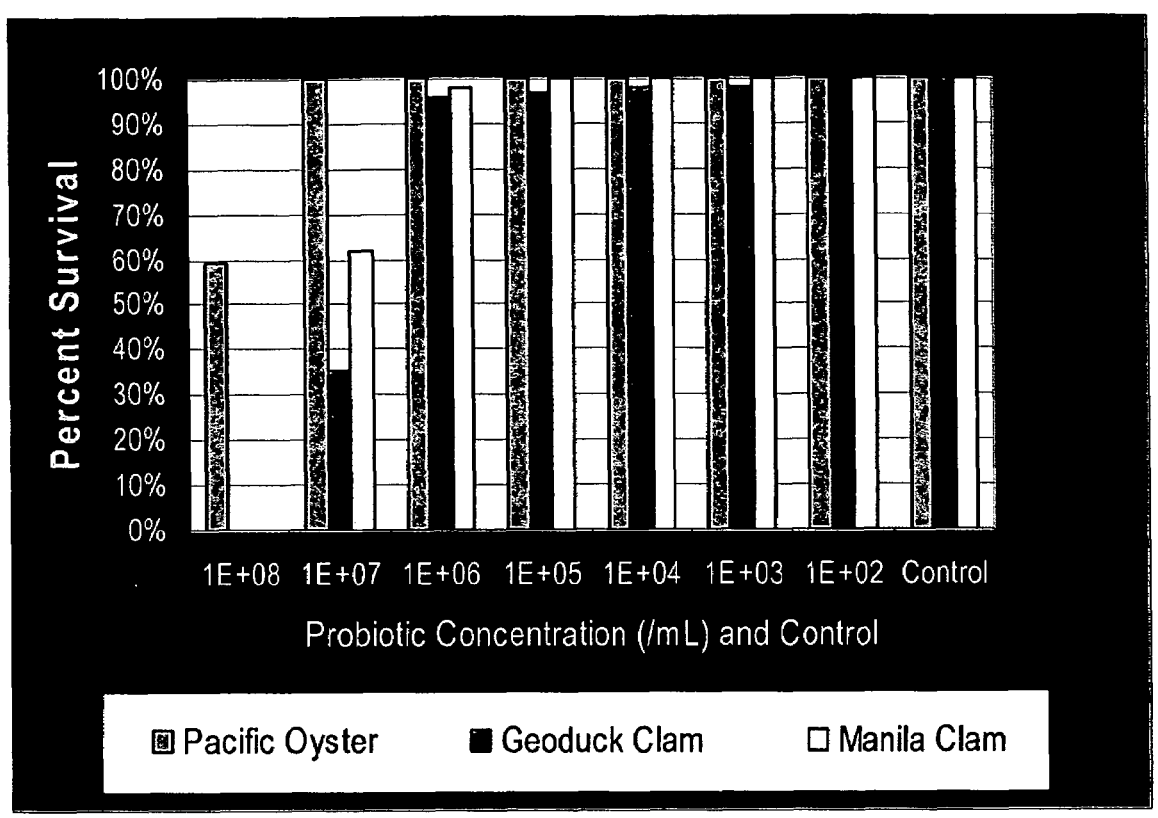
FIG. 2 shows a titration of the probiotic strain P02-45 against three species of bivalve larvae. Each bar is the average of three replicate cultures.

*philippinarum*) and geoduck clam (*Panope abrupta*) larvae (FIG. 2). The latter are known to be highly sensitive to pathogenic bacteria.

These experiments (FIG. 2) indicated that the probiotic strains were safe for these three species of larvae at concentrations of up to $10^6$ cfu/mL for manila clam and geoduck clams and $10^7$ cfu/mL for oysters, and that no pathogenic effects occurred. As we determined in subsequent experiments, there was never an instance in which the probiotic strains selected for characterization exceeded concentrations of $1 \times 10^5$ per mL in the seawater from larvae or juvenile cultures, when inoculated to achieve the determined working concentrations of from $10^4$ to $10^5$ cfu/mL.

Figure 5:
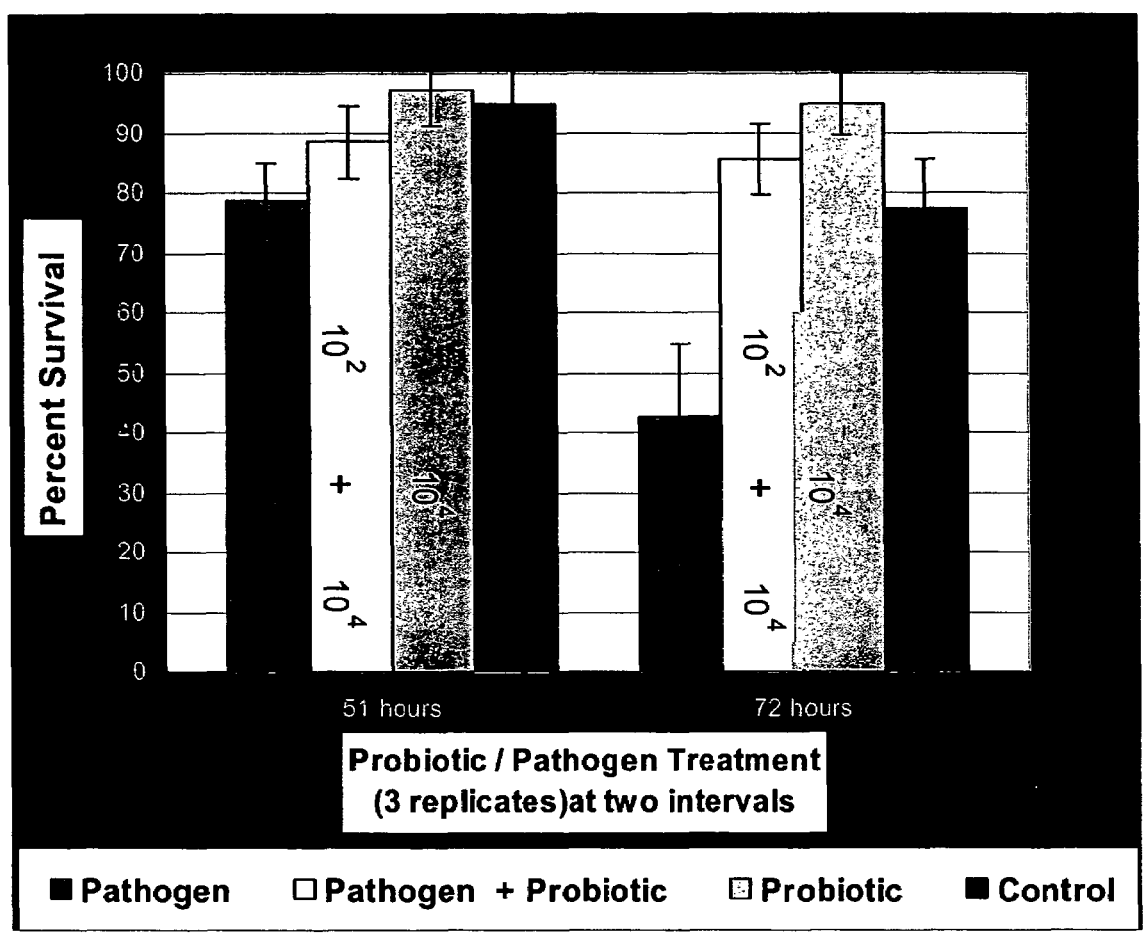
FIG. 5 shows improved survival of juvenile Pacific oysters exposed to pathogenic *Vibrio tubiashi* when treated with probiotic isolate P02-45. In addition, probiotic P02-45 added to juvenile oysters without pathogen challenge improved survival significantly in comparison to controls (P values in Tables 5 and 6.). The experiments were conducted in Petri dishes.

In all experiments, we were able to recover probiotic bacteria P02-1 and P02-45 from the cultures at the conclusion of the experiment. For the purposes of this study, recovery was based on visual identification of the isolated colonies which were distinctive from pathogens and from other isolates, which generally occurred at relatively low concentrations in cultures receiving probiotic bacteria (FIG. 5).

In a variety of pretreatments and repetitive additions of probiotic bacteria to larval cultures, the following results were found. Without pathogen added, we were always able to recover probiotic bacteria from the cultures, although we noted a stickiness of the bacteria and a propensity to attach to the culture container walls and the oyster larvae or juveniles. In a series of eight experiments as shown in Table 1, we determined that survival of oyster larvae was statistically significantly improved (an average of 32%) when probiotic bacteria were added to unchallenged groups of commercial hatchery-produced larvae at concentrations from $10^4$ to $10^5$ cfu/mL. In such cases probiotic bacteria were added on one occasion just prior to the addition of larvae to the test wells.

TABLE 1

Increased survival of unchallenged batches of Pacific oyster larvae from commercial hatcheries. Increments of improvement in probiotic treated groups from all experiments are statistically significant. The statistical analysis is described below in detail. All but experiment 7 consisted of direct single additions of probiotic. In experiment 7, larvae were fed Tahitian *Isochrysis* sp. at a concentration of 25,000 cells per mL containing probiotic bacteria at a concentration of about $5 \times 10^4$ P02-45 cfu/mL at the initiation of the experiment and at t = 24 hours.
Adding Probiotic Bacteria Increases Survival of Pacific Oyster Larvae

| Exper. Number | Probiotic Conc./mL | Time Evaluated (hours) | No. of Larvae in 3 reps | Control Survival | +Probiot Survival | Increased Survival Increment |
|---|---|---|---|---|---|---|
| 1 | $1.0 \times 10^5$ | 52 | 81 | 21% | 76% | 55% |
| 2A | $1.0 \times 10^5$ | 48 | 141 | 50% | 86% | 37% |
| 2B | $1.0 \times 10^4$ | 48 | 143 | 50% | 83% | 33% |
| 2C | $1.0 \times 10^3$ | 48 | 117 | 50% | 72% | 22% |
| 3 | $1.0 \times 10^4$ | 71 | 311 | 44% | 88% | 44% |
| 4 | $1.0 \times 10^4$ | 40 | 144 | 47% | 74% | 27% |
| 5 | $1.0 \times 10^5$ | 42 | 252 | 72% | 99% | 27% |
| 6 | $1.0 \times 10^5$ | 72 | 130 | 79% | 100% | 21% |
| 7 | In T. Iso × 3 | 50 | 92 | 22% | 38% | 15% |
| 8 | $1.0 \times 10^5$ | 68 | 244 | 44% | 86% | 42% |
| Average increased survival increment: | | | | | | 32% |

Figure 3:
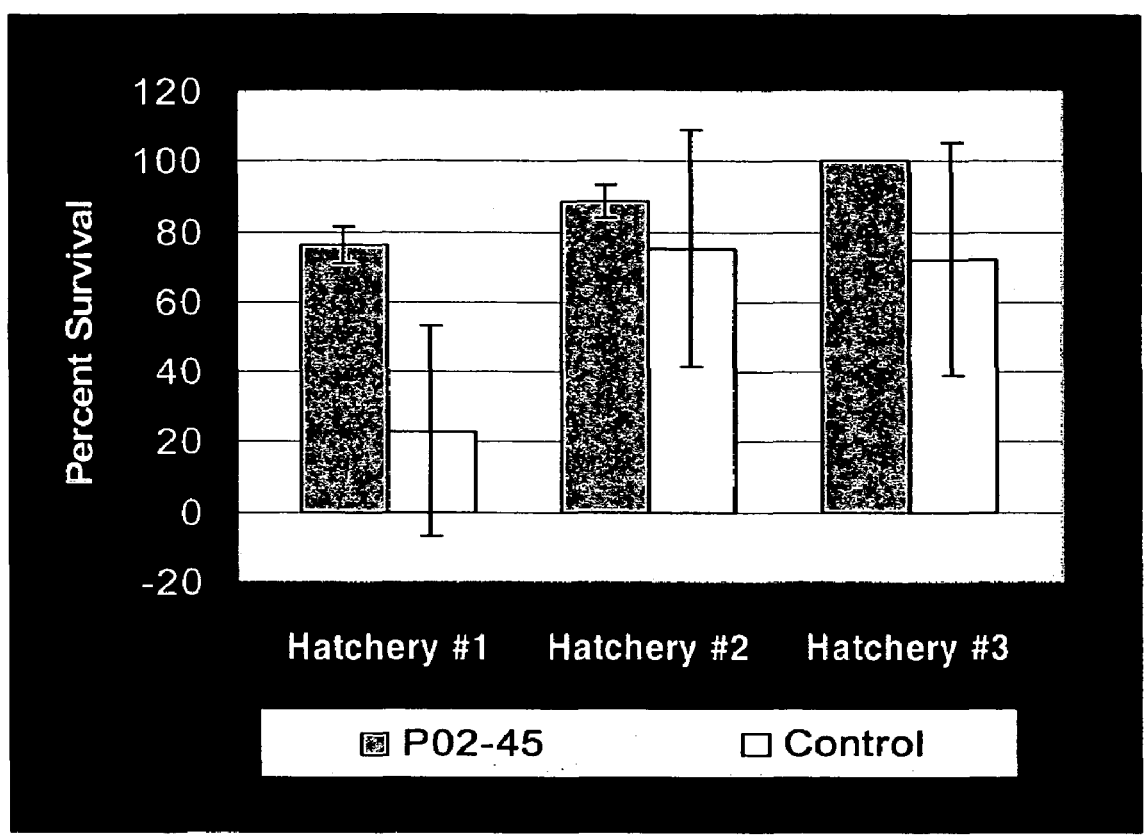
FIG. 3 shows an improvement in survival and reduced variability in survival resulting from addition of probiotic P02-45 to three production batches of oyster larvae in laboratory assays. 48 hour assay, 6 replicates per treatment. The brackets show 95% confidence intervals.

The results of this series of studies (Table 1) indicate that larvae obtained from three commercial hatcheries are colonized by bacteria that are mildly pathogenic or inhibitory and that replacement by the beneficial probiotic species results in two beneficial measured effects: (1) significant increase in survival and (2) decrease in variance among experimental groups. These results suggest that the two probiotic species we tested are successful in uniformly colonizing larval and juvenile cultures and preventing antagonistic, survival-depressing bacteria from becoming dominant. The decrease in variance, coupled with increased survival, among production batches of oyster larvae tested in the laboratory in additional experiments is shown in FIG. 3.

Statistical Analysis of Table 1 Data:

Based on the data given in Table 1, a hypothesis test was performed on the survival rate for each experiment as follows, using the first experiment as an example.

Let x denote the number of surviving larvae observed in the control group and y be the number of surviving larvae observed in the probiotic treatment group and let $p_x$ and $p_y$ denote the true survival rates of the larvae for the control group and probiotic group respectively. To test whether the larval survival rate of the probiotic group is significantly higher than that of the control group, the following hypotheses are formulated:

$$H_0: p_x = p_y \text{ vs } H_1: p_x < p_y.$$

The test statistic used here is:

$$z = \frac{\frac{x}{n} - \frac{y}{m}}{\sqrt{\frac{p^*(1-p^*)}{n} + \frac{p^*(1-p^*)}{m}}}$$

where $$p^* = \frac{x+y}{m+n}.$$

m and n are total numbers of larvae used in the probiotic group and control group respectively. In Experiment 1, we have observed m=n=81, x=17, y=62, and by using these numbers in the z-formula above we obtain the z-statistic as z=7.0025, which yields a P-value less than 0.001. Hence we can conclude that the larval survival rate of the probiotic group is significantly higher than that of the control group. The similar hypotheses pertaining to the other experiments were tested similarly and the results are summarized in Table 2.

TABLE 2

Summary of significance testing of Table 1 data.

| Experiment No. | z-value | P-value | Comment |
|---|---|---|---|
| 1 | 7.0025 | <0.001 | Extremely significant |
| 2A | 6.4845 | <0.001 | Extremely significant |
| 2B | 5.9245 | <0.001 | Extremely significant |
| 2C | 3.4517 | <0.001 | Extremely significant |
| 3 | 11.5890 | <0.001 | Extremely significant |
| 4 | 4.6921 | <0.001 | Extremely significant |
| 5 | 8.5631 | <0.001 | Extremely significant |
| 6 | 5.5500 | <0.001 | Extremely significant |
| 7 | 2.0968 | 0.018 | Very significant |
| 8 | 9.7235 | <0.001 | Extremely significant |

In is assumed that, within each group, the death of one larva does not affect another in our test. The z-statistic also provides more insight into the degree of significance. The higher the value of the z-statistic, the higher of the degree of significance.

We also made a comparison of the survival rates over all experiments evaluated using the average survival rate of the larvae for all control groups of 47.9% with a standard deviation of 18.2%. The average survival rate of the larvae from all probiotic groups is 80.0% with a standard deviation of 18.1%. The difference of 32.1% in the survival rates between the two groups is not only practically significant, but it is also proved to be statistically significant via a two-sample T-test. The T-value of the test is −3.95, the degrees of freedom are 17, and the P-value is equal to 0.001. In either case, we can conclude that the average survival rate of the larvae from the probiotic treated groups are significantly higher than that of the control groups.

Example 2

Challenge and Protection of Oyster Larvae and Juveniles by Probiotic Bacteria

We challenged Pacific oyster larvae and juveniles with two pathogens. The most virulent was a local isolate, designated X00-12-1, and a less virulent pathogenic isolate, designated NP-1 (new pathogen 1). The taxonomic affinities of the probiotic bacteria and NP-1 are based on fatty acid analysis and 16s rDNA sequencing.

Cultures receiving the highly virulent pathogen (isolate X00-12-1; likely synonymous with *Vibrio tubiashi* [Estes et al. 2004]) benefited from repetitive addition of the probiotic (Table 3). In these laboratory scale experiments, three additions of probiotic appeared optimal. In contrast, comparable protection could be provided by fewer or even single additions of the probiotic when oysters were challenged by the moderately pathogenic NP-1 or when probiotic was added to unchallenged larvae or juveniles. When analyzed statistically, using similar methods to those described in the preceding text, the differences between challenged larvae and challenged larvae with probiotic were highly significant (P values<0.01 to <0.001).

Figure 4:
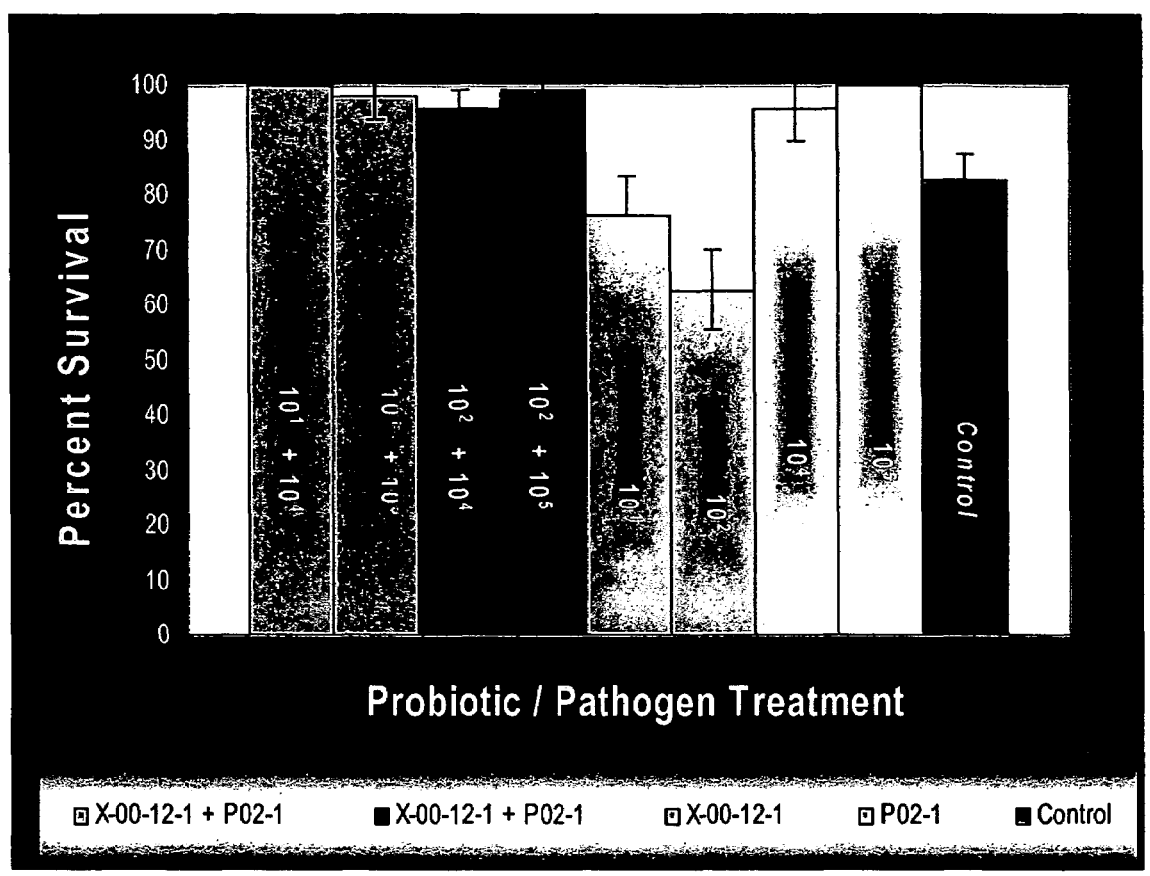
FIG. 4 shows that the survival of challenged and unchallenged Pacific oyster larvae is improved by treatment with probiotic isolate P02-1. Numbers in the four left hand bars indicate pathogen concentration (X-00-12-1; *Vibrio tubiashi*) followed by probiotic concentration. Six replicate well plates per treatment. Brackets indicate 95% confidence interval (where missing survival was 100% in all replicates). 48 hour assay.

FIG. 4 shows the protective effect of probiotic isolate P02-1 for Pacific oyster larvae challenged with *Vibrio tubiashi* in 6-well plates. In addition, the probiotic isolate significantly increased the survival of unchallenged larvae in comparison to control larvae. In a similar experiment, addition of probiotic P02-45 significantly improved the survival of juvenile Pacific oysters (shell length 1.5 to 2.5 mm) in comparison both to unchallenged controls and to groups challenged with *Vibrio tubiashi* (FIG. 5). The following is the statistical analysis of juvenile challenge data shown in FIG. 5.

TABLE 4

Survival data for juvenile oyster experiment at 51 hours and 72 hours

| | 51 hours | | | 72 hours | | |
|---|---|---|---|---|---|---|
| Treatments | Total Seed | Live Seed | Survival rate (%) | Total Seed | Live Seed | Survival rate (%) |
| Pathogen (X00-12-1) | 33 | 26 | 78.79 | 33 | 14 | 42.42 |
| Pathogen + Probiotic (X00-12-1 + P02-45) | 35 | 31 | 88.57 | 35 | 30 | 85.71 |
| Probiotic (P02-45) | 36 | 35 | 97.22 | 36 | 34 | 94.44 |
| Control | 37 | 35 | 94.59 | 40 | 31 | 77.50 |

Based on these survival data, the comparisons were done on both experiments using the similar approach described in the previous analysis (Table 2). In the 72 hours data, pathogen X00-12-1 treatment survival rate is lower than treatment X00-12-1+P02-45 survival rate. There was no significant difference of the survival rate between the two treatments in experiment at 51 hours post-inoculation, indicating that the

TABLE 3

Optimal direct addition of probiotic bacteria to larval oyster cultures challenged with virulent pathogen X00-12-01 (*Vibrio tubiashi*) consists of repetitive additions (representative data for most virulent pathogen). Single additions are beneficial to unchallenged larvae or to larvae challenged with the milder acting pathogen NP-1.

| Duration of Exper. (hours) | No. of Probiotic Additions | Addition Times (hours) | | | Conc. of Pathogen added | Conc. of Probiotic added | Larvae survival (%) | | Avg. Increase in Survival with Probiotic Added to Culture (%) |
|---|---|---|---|---|---|---|---|---|---|
| | | Probiotic | Larvae | Pathogen | | | Pathogen challenge only | Pathogen challenge + Probiotic | |
| 48 hrs | 1 | 0 | 4 | 5 | $1.0 \times 10^2$ | $1.0 \times 10^5$ | 8.5% | 31.9% | 23.4% |
| 48 hrs | 1 | 0 | 4 | 5 | $1.0 \times 10^2$ | $1.0 \times 10^5$ | 24.2% | 40.7% | 16.5% |
| 70 hrs | 3 | 0, 26, 50 | 24 | 28 | $1.0 \times 10^2$ | $1.0 \times 10^4$ | 2.5% | 97.5% | 95.0% |
| 70 hrs | 3 | 0, 26, 50 | 24 | 28 | $1.0 \times 10^2$ | $1.0 \times 10^3$ | 2.5% | 97.5% | 95.0% |
| 94 hrs | 4 | 0, 26, 50, 75 | 24 | 28 | $1.0 \times 10^2$ | $1.0 \times 10^4$ | 0.0% | 72.6% | 72.6% |
| 94 hrs | 4 | 0, 26, 50, 75 | 24 | 28 | $1.0 \times 10^2$ | $1.0 \times 10^3$ | 0.0% | 59.3% | 59.3% | pathogenic bacteria requires between 51 and 72 hours to cause disease in the juvenile shellfish

TABLE 5

Comparison of survival rates at 51 hours in juvenile challenge.

| Comparison | Difference in survival rate | z-value | P-value | Comment |
|---|---|---|---|---|
| Pathogen X00-12-1 vs Control | 15.80% | 1.97225 | 0.024 | X00-12-1's survival rate is significantly lower than control rate |
| X00-12-1 + P02-45 vs Control | 6.02% | 0.92423 | 0.177 | No significant difference |
| P02-45 vs Control | −2.63% | −0.56542 | 0.714 | No significant difference |
| X00-12-1 vs X00-12-1 + P02-45 | 9.78% | 1.09498 | 0.137 | No significant difference |

TABLE 6

Comparison of survival rates for juvenile challenge at 72 hours.

| Comparison | Difference in survival rate | z-value | P-value | Comment |
|---|---|---|---|---|
| X00-12-1 vs Control | 35.08% | 3.06740 | 0.001 | X00-12-1 survival rate is significantly lower than control rate |
| X00-12-1 + P02-4 vs Control | −8.21% | −0.91083 | 0.181 | No significant difference |
| P02-45 vs Control | −16.94 | −2.09634 | 0.018 | P02-45 rate is significantly higher than control rate |
| X00-12-1 vs X00-12-1 + P02-4 | 43.29% | 3.73337 | <0.001 | X00-12-1 rate is significantly lower than X00-12-1 + P02-45 rate |

Figure 6:
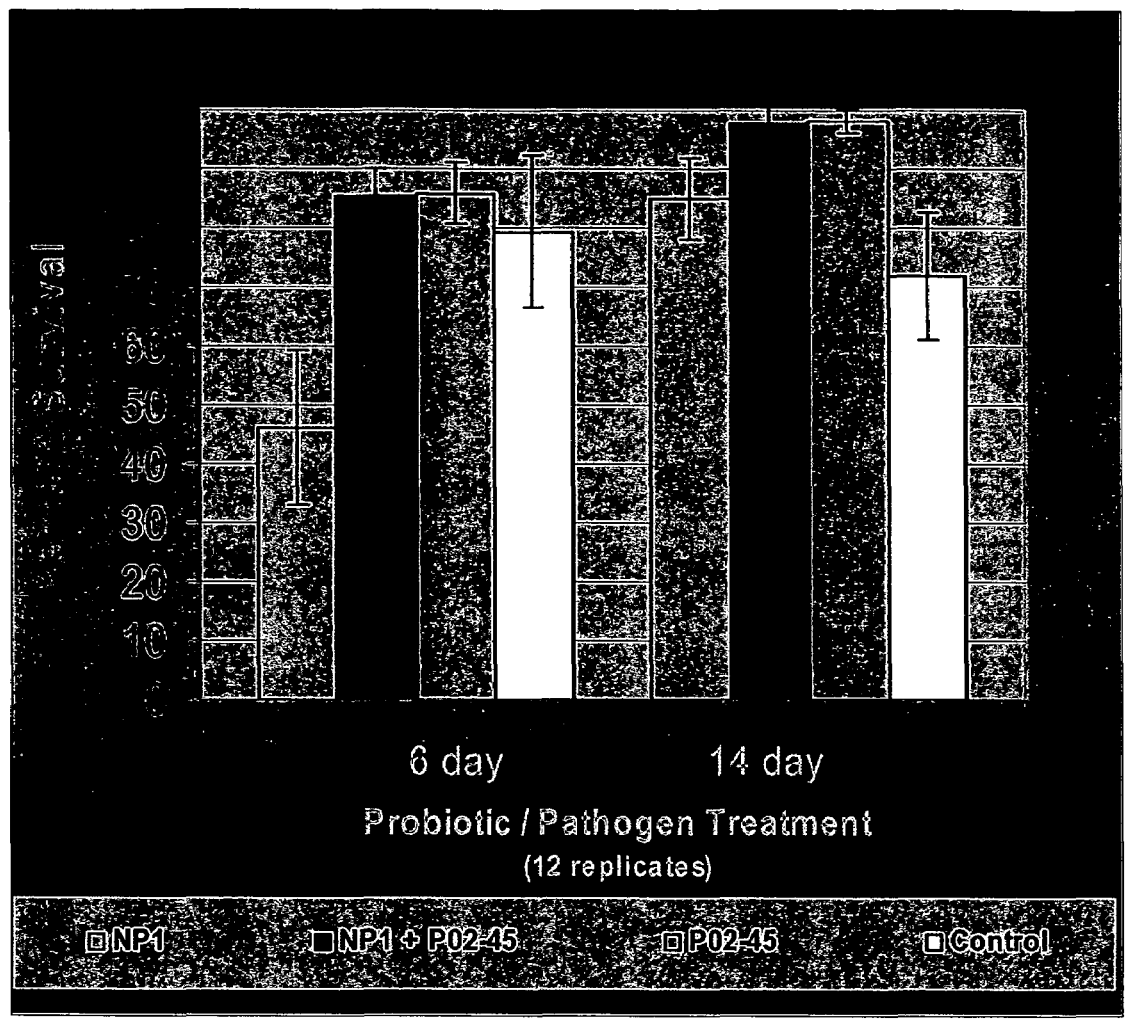
FIG. 6 shows protection of 6 day old and 14 day old Pacific oyster larvae challenged with pathogen NP-1. The probiotic significantly (see Table 7) increased survival in comparison to pathogen challenged 6 day old larvae. While the pathogenic effect was reduced in the 14 day old larvae, survival was still significantly improved by addition of probiotic P02-45, both in comparison to challenged and unchallenged control larvae.

Similar protection was provided in larval oysters challenged with pathogen NP-1. The results of challenging both 6 day old and 14 day old larvae with this pathogen and the beneficial effect of probiotic P02-45 are shown in FIG. 6. This experiment was continued for a total of 60 hours with similar statistically significant results, although survival in all groups declined, presumably due to lack of feeding in this experiment. We also tested pathogen NP-1 on juvenile oysters but found them refractory to challenge, consistent with the higher survival shown in 14 day old oyster larvae, as compared to 6 day old oyster larvae (FIG. 6).

Statistical Analysis of Larval Challenge Shown in FIG. 6

For the 6-day old larval challenge, using two-sample t-tests, we found that the NP1 pathogen treatment yielded a significantly lower survival rate than the control group while there exists no significant difference of survival rates between NP1+P02-45 and control, as well as between P02-45 and control. However, NP1's rate is found to be significantly lower than NP1+P02-45's rate, as shown in Tables 7 and 8.

TABLE 7

Comparison of survival rates for 6 day old larvae.

| Comparison | Difference in survival rate | t-value | P-value | Comment |
|---|---|---|---|---|
| NP1 vs Control | −33.24% | −3.54 | 0.002 | NP1 rate is significantly lower than control rate |
| NP1 + P02-45 vs Control | 5.88% | 0.84 | 0.417 | No significant difference |
| P02-45 vs Control | 6.27% | 0.89 | 0.391 | No significant difference |
| NP1 vs NP1 + P02-45 | −39.12% | −5.46 | <0.001 | NP1 rate is significantly lower than NP1 + P02-45 rate |

For the 14-day old larval challenge, we found that both NP1+P02-45 and P02-45 treatments yielded significantly higher survival rates than the control group while treatment NP1 only yields a marginally significant difference in comparing its survival rate with the control group. The larval survival rate in treatment NP1 is still found to be significantly lower than the larval survival rate in the NP1+P02-45 treatment.

TABLE 8

Comparison of survival rates for 14 day old larvae.

| Comparison | Difference in survival rate | t-value | P-value | Comment |
|---|---|---|---|---|
| NP1 vs Control | 13.19% | 2.03 | 0.058 | The difference is marginally significant |
| NP1 + P02-4 vs Control | 25.95% | 4.55 | 0.001 | NP1 + P02-45 is significantly higher than the control rate |
| P02-45 vs Control | 26.33% | 4.74 | 0.001 | P-02-45 is significantly higher than the control rate |
| NP1 vs NP1 + P02-4 | −12.76% | −3.28 | 0.005 | NP1 rate is significantly lower than NP1 + P02-45 rate |

Example 3

Co-Cultivation of Probiotic Bacteria with Unicellular Algal Foods

To study the co-cultivation of probiotic bacteria with algal food species, we ran a series of tests in 250 mL flasks incubated at 19° C. in a natural spectrum light incubator (24 hour light regime) with several probiotic candidates to determine compatibility with representatives of the various algal food species used in west coast shellfish hatcheries. Table 9 shows the initial screening results for co-cultivation of primary bacterial probiotic species and algal food species commonly used for feeding either larval or juvenile Pacific oysters and other early lifestage bivalve species. Algal and bacterial growth rates for selected compatible combinations were subsequently quantified in replicated (n=3) culture flasks.

TABLE 9

| Algal Food Species or Strain Designation | Probiotic Isolate Code and Initial Screening Results for Co-cultivation[1] | |
|---|---|---|
| | P02-1 | P02-45 |
| Tahitian *Isochrysis* sp. | + | + |
| *Chaetoceras calcitrans* | + | − |
| *Chaaetoceras gracilis* | − | + |
| *Rhodomonas* sp. (3C) | NT | + |
| *Tetraselmis* sp. (Plat P) | NT | + |
| *Tetraselmis* sp. (429) | + | + |
| *Thalassiosira pseudonana* (3H) | + | − |
| JDT (Hood Canal diatom) | NT | − |
| *Skeletonema costatum* | NT | − |
| *Pavlova lutheri* | NT | + |

[1] + = algal growth comparison by Coulter counter in treated and control cultures and probiotic bacteria recovered from 7 day static flask cultures;
− = no or limited visible algal growth in treated cultures, compared to control;
NT = Not tested.

Figure 7:
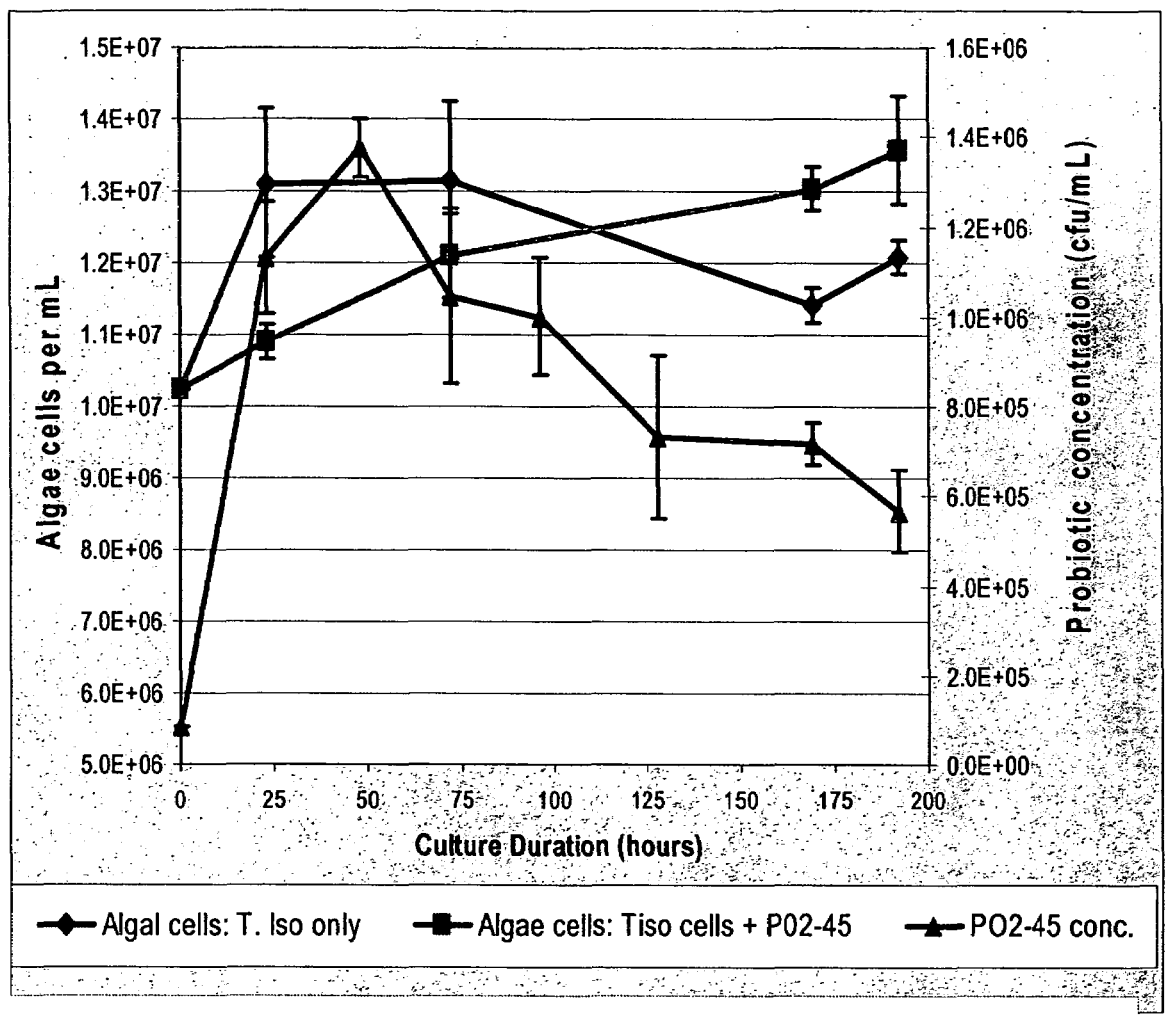
FIG. 7 shows a comparison of the growth of Tahitian *Isochrysis* sp. in 500 mL static flask cultures with and without the co-cultivation of probiotic P02-45. Concentrations of probiotic are shown. Average of three replicate flasks per treatment with brackets showing 95% confidence intervals.
Figure 8:
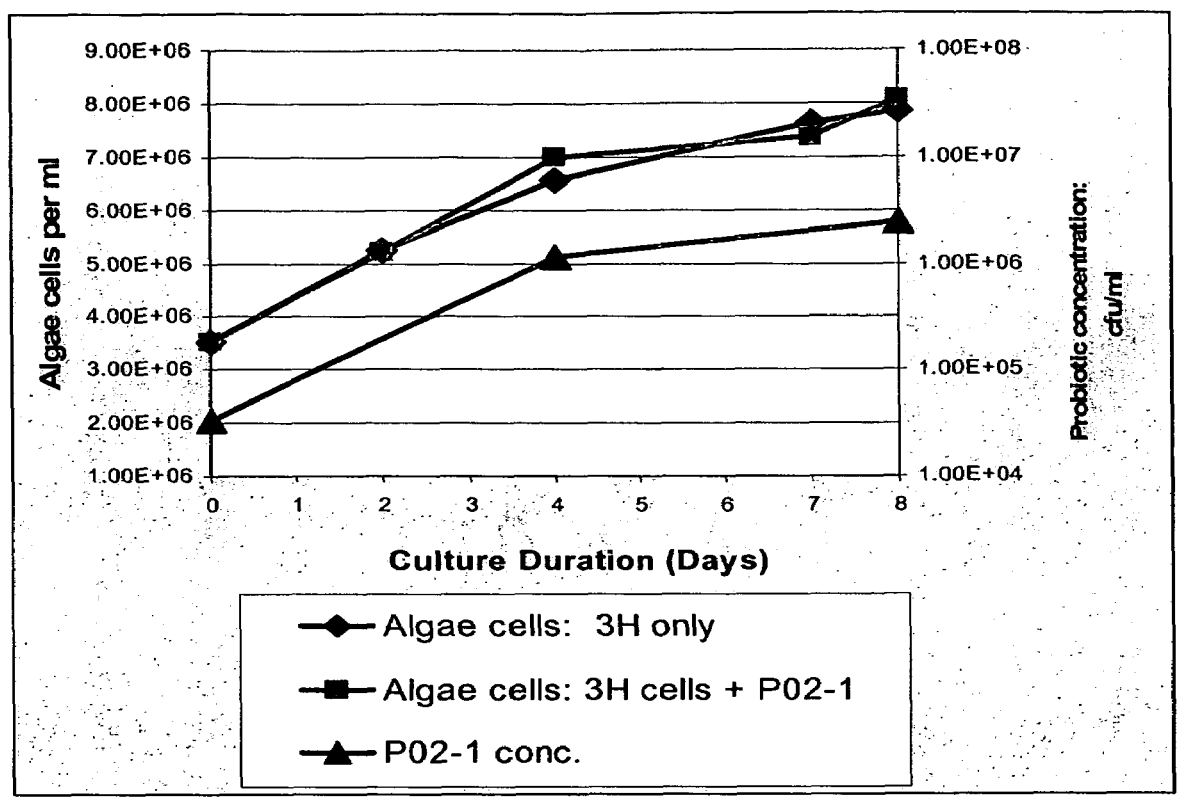
FIG. 8 shows a co-culture of algal food species diatom "3H" (*Thallasiosira pseudonana*) with probiotic P02-1.

This screening experiment clearly showed that some algal species are intolerant of the probiotic bacteria while others appeared to grow normally or at an improved rate in the presence of one or the other of the two primary selected probiotic bacteria. After seven days of incubation in the screening test, probiotic bacteria were recovered from all inoculated algal flasks. We then selected a sample of those algal species—probiotic combinations that appeared mutually tolerant and quantitatively evaluated growth of both the algae (by Coulter Counter enumeration) and the probiotic over a seven day period in triplicate cultures. Results for *T. Isochrysis* sp. are shown in FIG. 7. Similar replicated results were obtained for *Rhodomonas* sp. as shown in FIG. 7 for Tahitian *Isochrysis* sp. In another series of tests, we also found that *Thallasiosira pseudonana* (3H) was compatible with probiotic bacteria P02-1 (FIG. 8). This is a significant finding due to the importance of this species as a feed for later stage larvae and juvenile shellfish.

Figure 10:
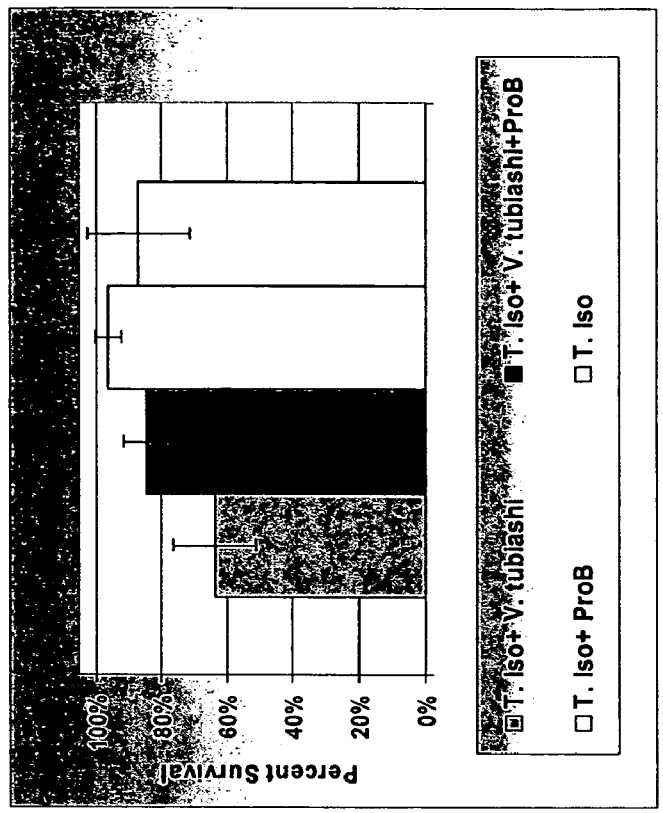
FIG. 10 shows significantly improved survival of Pacific oyster larvae challenged with *V. tubiashi* and fed *Tahitian Isochrysis* sp. co-cultivated with probiotic P02-1 in comparison to larvae fed algae only.
Figure 9:
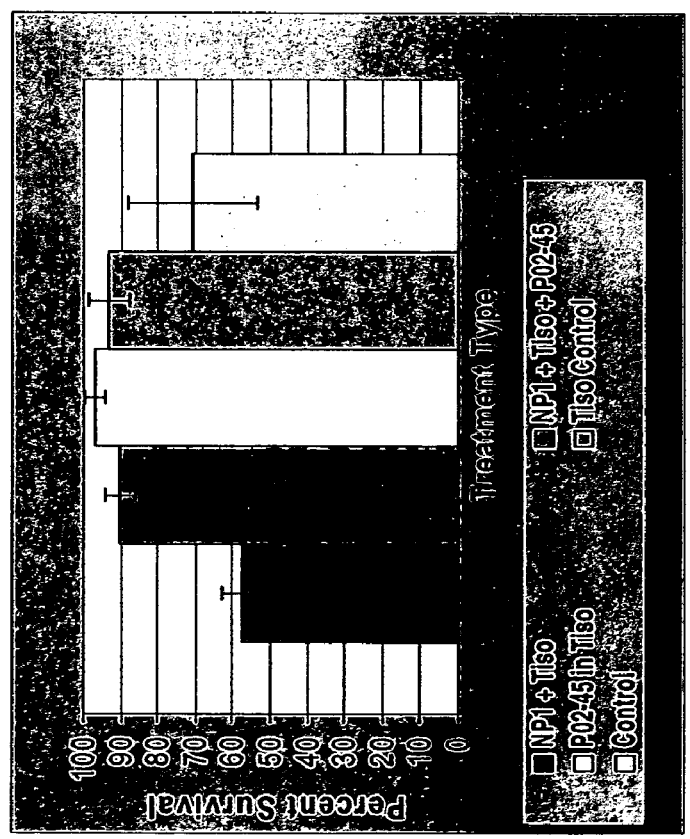
FIG. 9 shows significantly increased (P<0.01) survival in 10 day old oyster larvae fed *T. Isochrysis* grown with probiotic P02-45, when challenged by pathogen NP-1. 48 hour assay. 6 replicates per treatment.
Figure 11:
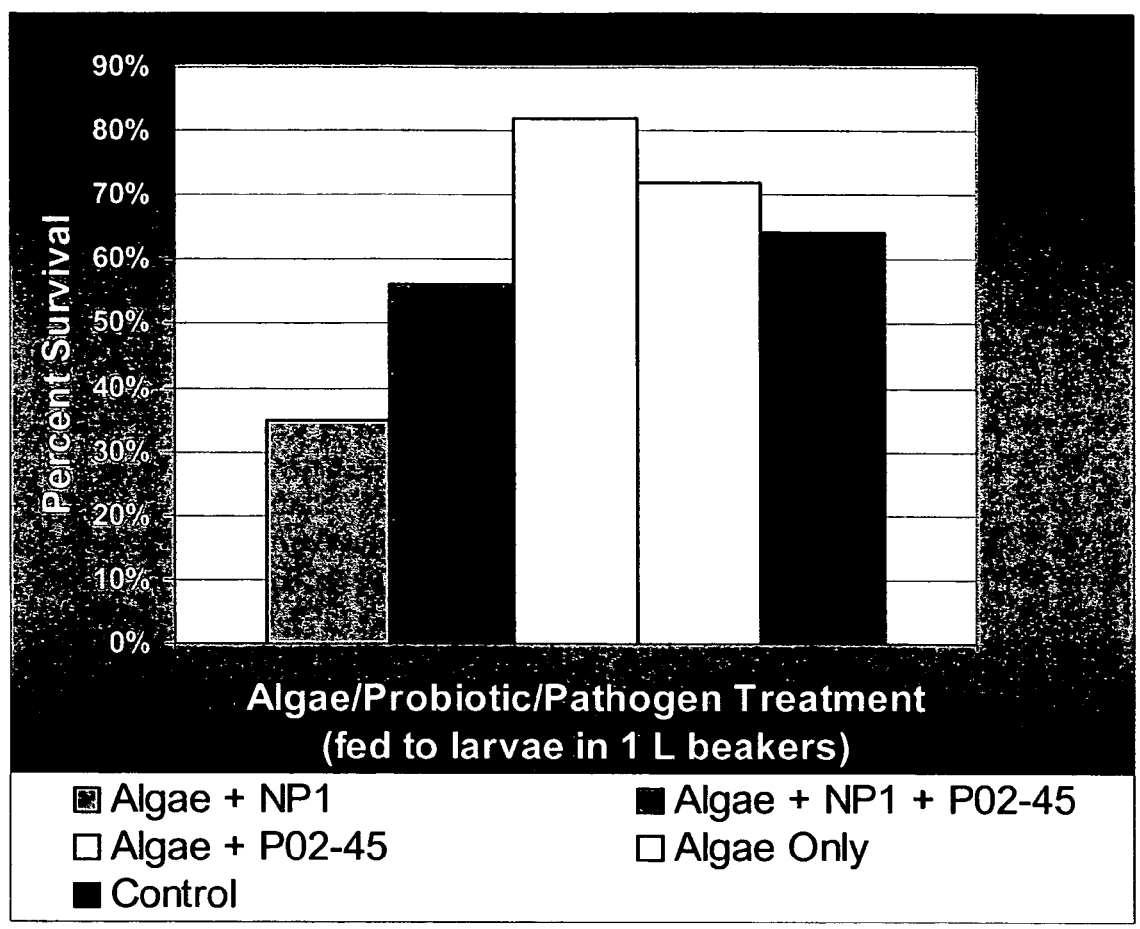
FIG. 11 shows improved survival of pathogen-challenged oyster larvae fed algal feed Tahitian *Isochrysis* sp. Co-cultivated with probiotic bacteria P02-45, in comparison to challenged larvae fed algae only. Treatments were tested in 1 L beakers. Results were measured after 48 hours.
Figure 12:
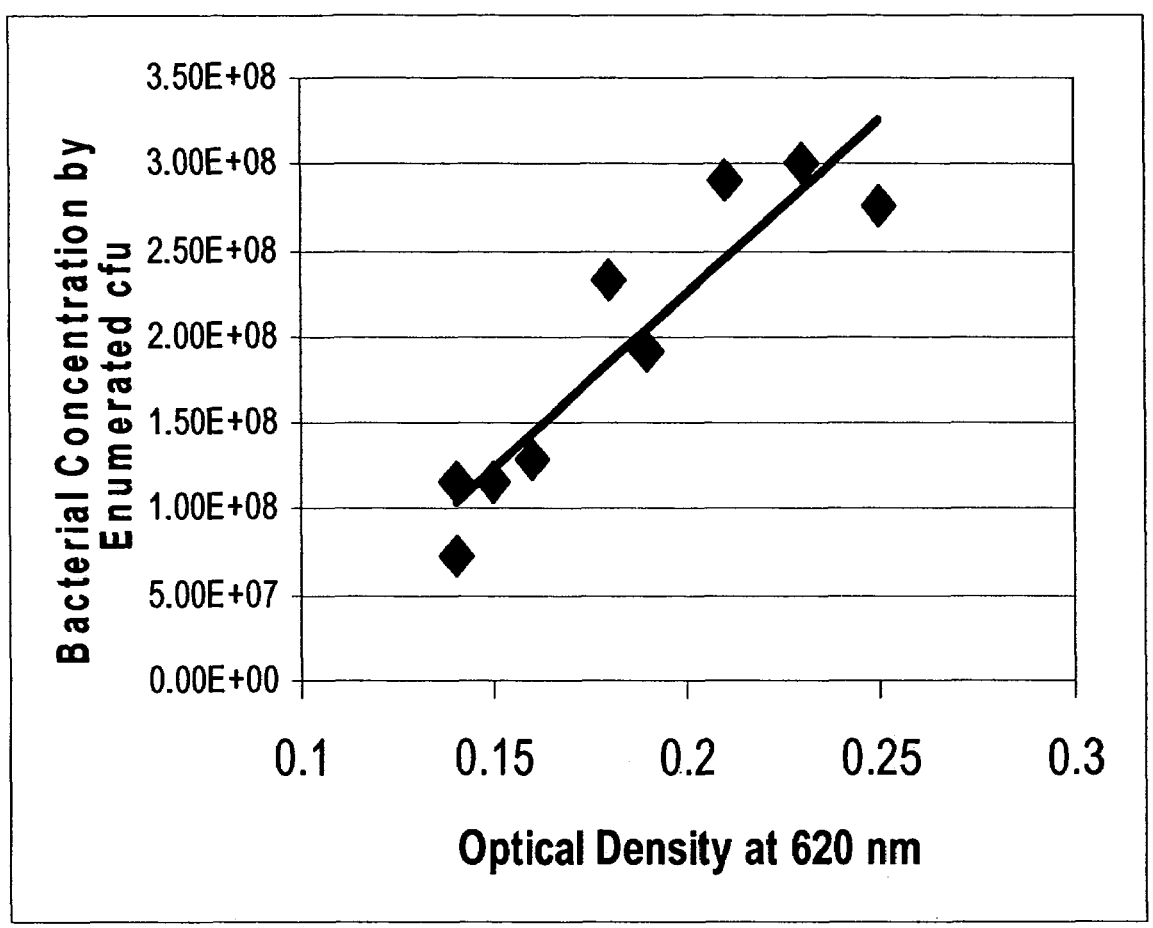
FIG. 12 is an example of relationship between optical density of probiotic P02-45 in sterile salt water and corresponding plate counts (cfu/mL).

We tested the ability of Tahitian *Isochrysis* sp. to act as a co-cultivar and vector for probiotic P02-45 in larval challenges. The results of these challenges show that in well plate experiments, larvae fed with Tahitian *Isochrysis* sp. grown with probiotic P02-45 survived at a significantly higher rate than those fed the same algal species grown without the probiotic bacteria. These replicated tests were conducted with both pathogens (FIGS. 9 and 10).

We then conducted an experiment in 1 liter beakers. The same trend of protection was shown in this experiment in that the larvae receiving probiotic P02-45 grown with Tahitian *Isochysis* sp. survived at a higher rate than pathogen challenged larvae fed the algal species without probiotic (FIG. 9). This experiment also provided an indication that the observations made in well plate experiments and Petri dishes were valid in larger, scaled up containers.

Example 4

Preparation of Probiotic Bacteria and Pathogens for Challenge Testing

Bacteria were grown on Marine Agar (Difco) for 24 to 48 hours at 25° C. Colonies were aseptically scraped and resuspended in sterile seawater. They were adjusted to a known concentration by light spectrophotometry absorbance at 620 nm, based on earlier calibration with plate count colony forming units (FIG. 10). It was important to thoroughly mix and resuspend the probiotic bacteria, due to their stickiness, in order to get consistent and uniformly diluted cfus in the plate counts. In addition, we determined that probiotic isolates P02-1 and P02-45 could be grown in diluted Marine Broth without marked reduction in yield.

REFERENCES CITED

Boettcher, J. J., B. J. Barber, J. T. Singer. 1999. Use of antibacterial agents to elucidate the etiology of juvenile oyster disease (JOD) in *Crassostrea virginica* and numerical dominance of an alpha-proteobacterium in JOD-affected animals. Appl. Environ. Microbiol. June 65(6): 2534-9.

Elston, R. A. and L. Leibovitz. 1980. Pathogenesis of experimental vibriosis in larval American oysters, *Crassostrea virginica*. Canadian Journal of Fisheries and Aquatic Sciences 37: 964-978.

Elston, R. A., E. L. Elliot and R. R. Colwell. 1982. Conchiolin infection and surface coating Vibrio: shell fragility, growth depression and mortalities in cultured oysters and clams, *Crassostrea virginica, Ostrea edulis* and *Mercenaria mercenaria*. Journal of Fish Diseases 5: 265-284.

Elston, R. A., P. Frelier and D. Cheney. 1999. Extrapallial abscesses associated with chronic bacterial infections in the intensively cultured juvenile Pacific oyster *Crassostrea gigas*. Diseases of Aquatic Organisms 37: 115-120.

Estes, R. M., Friedman, C. S., Elston, R. A., and Herwig, R. P. 2004. Pathogenicity testing of shellfish hatchery bacterial isolates on Pacific oyster *Crassostrea gigas* larvae. Diseases of Aquatic Organisms 58: 223-230.

From the foregoing, it will be appreciated that, although specific embodiments of the invention have been described herein for purposes of illustration, various modifications may be made without deviating from the spirit and the scope of the invention. Accordingly, the invention is not limited except as by the appended claims.

What is claimed is:

1. A biologically pure bacterial strain of bacteria *Pseudoalteromonas* P02-1 deposited as ATCC PTA-6677.

2. A method of inhibiting a pathogenic bacterial infection in marine organisms, comprising bathing a stock of marine organisms in a culture containing the bacterial strain of claim 1.

3. The method of claim 2 wherein said marine organisms are mollusks.

4. The method of claim 2, wherein the marine organisms are cultured food fish, including but not limited to salmon, trout, grouper, tuna fishes and all marine species whose early life stages may be reared under controlled conditions in seawater hatcheries and nurseries.

5. The method of claim 2 wherein said marine organisms are in the nauplii, larval, post-larval, or juvenile stage, or are adults or are brood stock.

6. A method of preventing growth of pathogenic bacteria by treatment of marine organism rearing tanks with bacterial strain of claim 1 prior to the introduction of marine organisms to the tank.

7. A composition comprising the bacterial strain of claim 1 and a culture selected from the group consisting of unicellular algae and multi-cellular algae.

8. A biologically pure bacterial strain of bacteria *Pseudoalteromonas* P02-45 deposited as ATCC PTA-6678.

9. A method of inhibiting a pathogenic bacterial infection in marine organisms, comprising bathing a stock of marine organisms in a culture containing the bacterial strain of claim 8.

10. The method of claim 9 wherein said marine organisms are mollusks.

11. The method of claim 9, wherein the marine organisms are cultured food fish, including but not limited to salmon, trout, grouper, tuna fishes and all species whose early life stages may be reared under controlled conditions in seawater hatcheries and nurseries.

12. A method of preventing growth of pathogenic bacteria by treatment of marine organism rearing tanks with bacterial strain of claim 8 prior to the introduction of marine organisms to the tank.

13. A composition comprising the bacterial strain of claim 8 and a culture selected from the group consisting of unicellular algae and multi-cellular algae.

14. A composition comprising a mixture of biologically pure bacterial strains *Pseudoalteromonas* P02-1 deposited as ATCC PTA-6677 and *Pseudoalteromonas* P02-45 deposited as ATCC PTA-6678 wherein said mixture contains between 1% and 99% colony forming units of strain *Pseudoalteromonas* P02-1 deposited as ATCC PTA-6677 and between 1% and 99% colony forming units of strain P02-45 deposited as ATCC PTA-6678.

15. A method of inhibiting a pathogenic bacterial infection in marine organisms, comprising bathing a stock of said marine organisms in a culture containing the composition of claim 14.

16. The method of claim 15 wherein said marine organisms are mollusks.

17. The method of claim 15, wherein the marine organisms are cultured food fish, including but not limited to salmon, trout, grouper, tuna fishes and all species whose early life stages may be reared under controlled conditions in seawater hatcheries and nurseries.

18. A method of preventing growth of pathogenic bacteria in commercial and residential salt water aquariums wherein the aquarium is treated with bacterial strain *Pseudoalteromonas* P02-1 deposited as ATCC PTA-6677, P02-45 deposited as ATCC PTA-6678, or a mixture thereof.

* * * * *

UNITED STATES PATENT AND TRADEMARK OFFICE
CERTIFICATE OF CORRECTION

PATENT NO. : 7,407,652 B2  
APPLICATION NO. : 11/144929  
DATED : August 5, 2008  
INVENTOR(S) : Ralph A. Elston, Arthur Gee and Karen L. Humphrey It is certified that error appears in the above-identified patent and that said Letters Patent is hereby corrected as shown below:

Title Pg, Item (73) Assignee: should read as follows:

(73) Assignee: AquaTechnics Inc., Sequim, Wa (US).

Signed and Sealed this

Twenty-eighth Day of October, 2008

JON W. DUDAS  
*Director of the United States Patent and Trademark Office*